United States Patent [19]

Wade

[11] Patent Number: 5,141,841
[45] Date of Patent: Aug. 25, 1992

[54] RADIATION SENSITIVE COMPOUND

[75] Inventor: John R. Wade, Otley, United Kingdom

[73] Assignee: Vickers PLC, London, United Kingdom

[21] Appl. No.: 395,218

[22] Filed: Aug. 17, 1989

Related U.S. Application Data

[63] Continuation of Ser. No. 275,699, Nov. 23, 1988, abandoned, which is a continuation of Ser. No. 111,141, Oct. 16, 1987, abandoned, which is a continuation of Ser. No. 936,988, Dec. 2, 1986, abandoned, which is a continuation of Ser. No. 639,908, Aug. 10, 1984, abandoned.

[30] Foreign Application Priority Data

Aug. 12, 1983 [GB] United Kingdom ............... 8321813

[51] Int. Cl.$^5$ .............. G03F 7/028; G03F 7/039; G03C 1/675
[52] U.S. Cl. ........................ 430/281; 430/920; 430/923; 430/916; 430/924; 430/925; 430/926; 430/191; 430/270; 430/343; 430/344; 522/34; 522/45; 522/52
[58] Field of Search .............. 430/281, 920, 923, 916, 430/924, 925, 926, 191, 270, 343, 344; 522/34, 45, 52

[56] References Cited

U.S. PATENT DOCUMENTS

| | | | |
|---|---|---|---|
| 3,859,098 | 1/1975 | Iwama et al. | 430/925 |
| 3,870,524 | 3/1975 | Watanabe et al. | 430/281 |
| 3,987,037 | 10/1976 | Bonham et al. | 430/343 |
| 4,043,887 | 8/1977 | Pacifici et al. | 430/281 |
| 4,053,316 | 10/1977 | Lu | 430/923 |
| 4,058,398 | 11/1977 | Osada et al. | 430/920 |
| 4,119,466 | 10/1978 | Van Allan et al. | 96/115 |
| 4,189,323 | 2/1980 | Buhr | 430/281 |
| 4,239,850 | 12/1980 | Kita et al. | 522/34 |
| 4,258,123 | 3/1981 | Nagashima et al. | 430/920 |
| 4,505,793 | 3/1985 | Tamoto et al. | 430/920 |
| 4,619,998 | 10/1986 | Buhr | 430/281 |

FOREIGN PATENT DOCUMENTS 32613 7/1981 European Pat. Off. .

Primary Examiner—Cynthia Hamilton
Attorney, Agent, or Firm—Spensley Horn Jubas & Lubitz

[57] ABSTRACT

A radiation-sensitive compound has the general formula

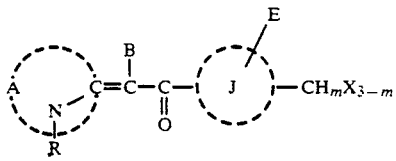

wherein
A represents the ring members required to complete a 5- or 6-membered heterocyclic ring which may optionally be fused to an optionally substituted aromatic nucleus,
B represents H, acyl, aroyl, heterocyclyl carbonyl or

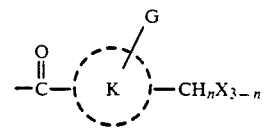

R represents an optionally substituted alkyl group,
E and G, which may be the same or different, each represents H or $CH_pX_{3-p}$,
J and K, which may be the same or different, each represents an aryl or heterocyclic group, which may optionally include a substituent additional to E or G,
X represents Cl or Br, and m,n and p, which may be the same or different, each represents an integer equal to 0, 1 or 2.

The compound can be used to form radiation sensitive compositions for the production of radiation sensitive plates in lithographic printing plate manufacture.

8 Claims, No Drawings

RADIATION SENSITIVE COMPOUND

This is a continuation of application Ser. No. 07/275,699, filed Nov. 23, 1988, abandoned, which in turn is a continuation of application Ser. No. 07/111,141, filed on Oct. 16, 1987 abandoned, which in turn is a continuation of application Ser. No. 06/936,988 filed on Dec. 2, 1986 abandoned, which in turn is a continuation of application Ser. No. 06/639,908, filed on Aug. 10, 1984 abandoned.

This invention relates to radiation-sensitive compounds, to radiation sensitive compositions containing such compounds and to radiation-sensitive devices, in particular, radiation sensitive plates for lithographic printing plate production, photoresists and photo-imaging systems, incorporating such radiation sensitive compositions.

According to the invention, there is provided a radiation-sensitive compound having the general formula

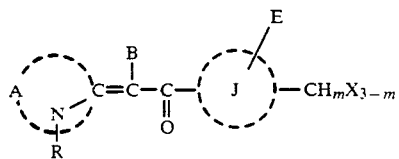

wherein

A represents the ring members required to complete a 5- or 6-membered heterocyclic ring which may optionally be fused to an optionally substituted aromatic nucleus, B represents H, acyl, aroyl, heterocyclyl carbonyl or

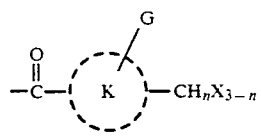

R represents an optionally substituted alkyl group,

E and G, which may be the same or different, each represents H or $CH_pX_{3-p}$, J and K, which may be the same or different, each represents an aryl or heterocyclic group, which may optionally include a substituent additional to E or G, X represents Cl or Br, and m,n and p, which may be the same or different, each represents an integer equal to 0, 1 or 2.

Examples of groupings of the type where the heterocyclic ring is fused to an aromatic nuclei are benzothiazoline, benzoselenazoline, benzoxazoline, naphthothiazoline, naphthoselenazoline and naphthoxazoline groups.

Specific examples of compounds in accordance with the present invention are shown in Formulae I to XXII. Particularly preferred compounds are 3-methyl-2-(4'-trichloromethylbenzoylmethylene)-benzothiazoline (Formula I; 3-methyl-2-(4'-trichloromethylbenzoylmethylene)-benzoselenazoline (Formula IV); 3-ethyl-2-(4'-trichloromethylbenzoylmethylene)-naphtho(1,2-d)thiazoline (Formula V); 3-methyl-2,2-bis-(4'-trichloromethylbenzoylmethylene)-benzothiazoline (Formula III); 1,3,3-trimethyl-2-(4'-trichloromethyl benzoyl) methylene indoline (Formula VIII); 1,3,3,-trimethyl-2-(4'-trichloromethyl benzoyl)methylene-5-chloro-indoline (Formula IX); and 1-methyl-2-(4'-trichloromethyl benzoyl methylene)-quinoline (Formula XV).

The compounds of the invention are sensitive to radiation having a wavelength in the range of from 300 to 550 nm. Coherent radiation from a laser in the same range can also be used, as can an electron beam.

The compounds of the present invention may be prepared by reacting a methylene base derivative of a heterocyclic compound of the formula

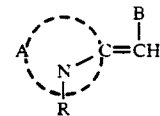

with an acid halide of formula

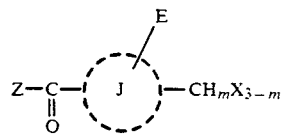

where Z is halogen and A,B,R,E,J,X and m have the above meanings by procedures similar to those described in British Patent Specification No.498012.

Alternatively, if the methylene base is not readily available, the compounds may be prepared by reacting a quaternary heterocyclic salt of formula

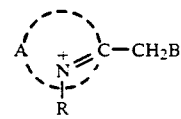

with the acid halide in the presence of an acid binding agent (e.g. an amine, preferably triethylamine or pyridine) by procedures similar to those described in U.S. Pat. Nos. 2112139 and 4119466.

The following syntheses are typical Preparation of 3-methyl-2-(4'-trichloromethylbenzoyl methylene)-benzothiazoline (Formula I)

2,3-dimethylbenzothiazolinium-p-toluene sulphonate (10 g) was slurried in dry toluene (50 ml) and cooled to 5 degC. A solution of 4-trichloromethylbenzoyl chloride (8.9 g) in dry toluene (10 ml) was added dropwise to the stirred slurry over a period of 30 minutes, maintaining the temperature at 10–15 degC. A solution of triethylamine (7 ml) in dry toluene (10 ml) was then added dropwise over a period of 30 minutes, the temperature again being maintained at 10–15 degC. The reaction mixture was stirred for two hours at room temperature. The solid product was filtered off, reslurried in methanol and recrystallised from a 3/1 chloroform/methanol solution.

The final yield was 3.1 g of a product having a melting point of 170-171 degC and a max. of 394 nm.

Elemental analysis Figures were:
Theory: C 53.06; H 3.12; N 3.64%
Found: C 53.21; H 3.32; N 3.79%

Preparation of
3-methyl-2,2-bis(4'-trichloromethylbenzoylmethylene)-
benzothiazoline (Formula III)

2,3-dimethylbenzothiazolium-p-toluene sulphonate (6.7 g) and 4-trichloromethylbenzoyl chloride (11.9 g) were dissolved in dry pyridine (40 ml), with stirring. The solution was heated to 70-80 degC and maintained within this temperature range for two hours before allowing it to cool to room temperature overnight. Methanol (200 ml) was added to the reaction mixture followed by sufficient water to cause the product to precipitate. The crude product was filtered off and washed with hot methanol to give 2.5 g of a product having a melting point of 148-149 degC and a λ max. of 375 nm. Elemental analysis Figures were:
Theory: C 49.50; H 2.47; N 2.31%
Found: C 50.36; H 2.65; N 2.55%

Preparation of 1,3,3-trimethyl-2-(4'-trichloromethyl benzoyl) methylene 5-chloro indoline (Formula IX)

To a stirred solution of 5-chloro-1,3,3-tri methyleneindoline (9.35 g) in dry toluene (40 ml) was added, dropwise, a solution of 4-trichloromethylbenzoyl chloride (11.61 g) in dry toluene (30 ml). When the addition was complete, the mixture was heated to 6020 C. and maintained at this temperature for 1½ hours before filtering (hot). A red solid was obtained from the toluene filtrates after removal of solvent on a rotary evaporator. The crude product was slurried in ethyl alcohol, filtered and washed with ethyl alcohol to give 7.3 g of a pale yellow crystalline solid having a melting point of 152°-153° C. and a λ max (MeOH) of 392 nm.
Elemental analysis figures were
Theory : C 55.94; H 3.96; N 3.26%
Found: C 55.96; H 4.16; N 3.29%

The compounds of the invention act as free radical generators and as acid release agents. It is believed that, when exposed to actinic radiation, the compounds dissociate to form a free radical and a halogen atom which produces acid when hydrogen donors are present. The effectiveness of a particular compound as an initiator can be used as a measure of its effectiveness in mechanisms depending on the presence of acid.

The compounds have a wide range of application.

The compounds may be used to produce radiation sensitive compositions. Generally, an amount of the compound as low as 0.4% by wt. of the solids content of the composition (preferably from 0.5 to 7%) is effective.

In one embodiment the radiation sensitive composition may comprise a compound of the present invention and a photopolymerisable material activated by free radicals. In this case, the compound of the present invention acts as a photoinitiator for the material on exposure to radiation. Particularly suitable materials for producing such radiation sensitive compositions are addition polymerisable compounds containing ethylenic unsaturation. Preferred are simple compounds, or monomers as they are sometimes denominated, containing ethylenic unsaturation, as well as polymers containing end groups or pendant groups terminating with ethylenic unsaturation. For example, the phrase "addition polymerisable compound" is intended to include polymers having recurring units with the structure

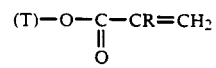

wherein T is any group capable of forming the backbone of a polymer and R is hydrogen or methyl.

Other examples of useful addition polymerisable compounds containing ethylenic unsaturation include monomeric (meth)acrylates, (meth)acrylamides, allyl compounds, vinyl ethers, vinyl esters, N-vinyl compounds, styrenes, acrylonitriles and crotonates. Many examples of each of these classes are well known, such as those listed for example in British Patent Specification No.1534137.

A highly preferred class of addition polymerisable compounds containing ethylenic unsaturation encompasses the (meth)acrylate compounds. Particularly useful examples include alkyl (meth)acrylates containing from 1 to 30 and most preferably 1 to 5 carbon atoms in the alkyl portion, such as methyl and ethyl (meth)acrylate; pentaerythritol tri-and tetra (meth)acrylates; esters of polyols including glycol di(meth)acrylates, such as tripropylene glycol diacryalate, tetraethylene glycol diacrylate and triethylene glycol dimethacrylate; alkanediol di(meth)acrylates such as hexanediol di(meth)acrylates; polyether di(meth)acrylates; urethane (meth)acrylates such as the reaction products of hydroxyl group containing (meth)acrylates with di or polyisocyanates; epoxy (meth)acrylates; and mixtures of the above.

In accordance with another embodiment, the radiation sensitive composition comprises a compound of the present invention and an acid hardenable material. In this case, the acid released during photolysis of the compound of the present invention catalyses the polymerisation of the acid hardenable material. Suitable acid hardenable materials are for example, epoxy resins, phenol/formaldehyde resins, amino-plastics such as urea/formaldehyde and melamine/formaldehyde resins, vinyl ethers and N-vinyl compounds. (In the case of the latter two materials, it may be that radical initiated reactions could take place).

In accordance with a further embodiment, the radiation sensitive composition comprises a compound of the present invention and an acid degradable compound. Such a radiation sensitive composition is positive working in that, on exposure, the radiation struck areas become solubilised relative to the non-radiation struck areas. Examples of suitable acid degradable compounds are acetals as disclosed in GB Patent Specification No.1548757 and U.S. Pat No. 3782939, oxycarbonyl esters of phenols as disclosed in European Patent Specification 102450, and polyaldehydes as disclosed in U.S. Pat. No. 3984253.

In accordance with yet a further embodiment, the radiation sensitive composition comprises a compound of the present invention and a substance which exhibits a colour change when the compound is exposed to radiation. Thus, the substance may be a dye, dye precursor or indicator which becomes bleached or otherwise changes colour in the presence of the acidic photolysis products of the compound of the present invention or a leuco dye which is caused to become coloured by oxidation as a consequence of the exposure to radiation of the compound.

Such colour changes are particularly important in the production of lithographic printing plates from radiation sensitive plates since they provide a visible distinction between the image and non-image areas after image-wise exposure that allows defects to be noticed before the plate is developed.

A radiation sensitive composition comprising a compound in accordance with the invention may be coated onto a substrate to form a radiation sensitive plate. Such plates may be used in lithographic printing plate production. In this case, the composition is image-wise exposed to actinic radiation so that parts of the composition are struck by radiation and parts are not. Depending upon the nature of the other components of the radiation sensitive composition, those parts which are radiation-struck have increased or reduced solubility in developer liquids compared to the non-radiation struck parts. Thus by developing the image-wise exposed composition using such a liquid, the more soluble parts are selectively removed and an image constituted by the less soluble parts remains on the substrate. The image constitutes the water repellent ink receptive printing area of the lithographic printing plate and the water receptive ink repellent non-printing area of the lithographic printing plate is constituted by the surface of the substrate revealed during the development step.

In a similar way, a radiation sensitive composition may be coated on to a substrate and be image-wise exposed and developed when it is desired to use the composition as a photoresist.

The substrate used in the foregoing may be any substrate conventionally used with photoresists or in the production of lithographic printing plates and a substrate formed of grained and anodised aluminum is particularly preferred.

If desired, a polymeric binder may be incorporated in the radiation sensitive composition to strengthen the composition and improve the adherence of the composition to the substrate. Typical binders are acrylic polymers, vinyl acetate polymers, and novolak resins. Many examples of suitable polymers are listed in the patent literature and reference may be made for example, to U.S. Pat. Nos. 3 652 275 and 4 268 667 and GB published Patent Application No.2 006 775.

The polymerisation of vinyl group containing monomers is inhibited by the presence of oxygen. It is therefore desirable to provide, over coatings of radiation sensitive compositions comprising such monomers, a barrier layer which is transparent to radiation and also impervious to oxygen. A layer of polyvinyl alcohol is particularly suitable for this purpose.

The following Examples illustrate the invention.

EXAMPLE 1

An electrolytically grained and anodised aluminum sheet was whirler coated with a solution, in ethyl methyl ketone, of a radiation sensitive composition comprising:
  3 parts by weight of the dimethacrylate ester of the glycidyl ether of Bisphenol A,
  1 part by weight of a vinyl acetate/crotonic acid copolymer, and
  0.15 parts by weight of the compound of Formula I, the coating weight was 1 gm. per sq.m. After drying, an overcoating of poly(vinyl alcohol) was applied to prevent oxygen inhibition. The resultant radiation sensitive plate was exposed through a continuous tone Stouffer step-wedge to ultra-violet light (0.5 units) from a Berkey-Ascor printing down frame and developed with an aqueous solution containing sodium propanoate, sodium benzoate and a surfactant. The developed image of the resultant lithographic printing plate had a step-wedge of solid 8 tail 13.

EXAMPLE 2

Example 1 was repeated using the compounds of Formulae II to XXII. The Example was then repeated twice more using, in one case, an exposure of 5 units in the absence of the overcoating and using, in the other case, an exposure of 5 units in the presence of the overcoating.

The following Table gives details of the melting point (where known) and λ max. for these compounds and the speeds of the radiation sensitive plates derived from them. In the table, the designation "o/c" signifies that the overcoating was used and the designation "no o/c" signifies that the overcoating was omitted.

TABLE

| Compound | M.P. (°C.) | λmax | Speed (solid,tail) 0.5 units (o/c) | 5 units (no o/c) | 5 units (o/c) |
|---|---|---|---|---|---|
| II | 165–166 | 386 | — | — | 8,14 |
| III | 148–149 | 375 | 4,7 | 2,8 | — |
| IV | 177–180 | 394 | 7,13 | 7,15 | — |
| V | 210 decomp. | 409 | 7,12 | 8,14 | — |
| VI | 169–170 | 374 | 3,9 | 5,13 | — |
| VII | 206–207 | 410 | 8,13 | 8,13 | — |
| VIII | 147–148 | 392 | 6,11 | 7,15 | — |
| IX | 152–153 | 392 | 9,13 | 9,15 | — |
| X | 205–206 | 416 | 2,8 | 1,8 | — |
| XI | 159–160 | 386 | — | — | 7,12 |
| XII | 168–170 | 389 | 7,12 | 6,14 | — |
| XIII | 110 | 390 | — | — | 8,14 |
| XIV | 170 decomp. | 387 | — | — | 7,13 |
| XV | 183 decomp. | 435 | — | — | 5,10 |
| XVI | >250 | 384 | — | — | 8,13 |
| XVII | — | 398 | — | — | 4,11 |
| XVIII | — | 392 | 5,12 | 3,11 | — |
| XIX | — | 395 | — | 1,6 | 9,16 |
| XX | — | 382 | — | — | 5,12 |
| XXI | — | 411 | 9,15 | 7,15 | — |
| XXII | — | 403 | 6,13 | 5,11 | — |

EXAMPLE 3

Example 1 was repeated except that the radiation sensitive composition also contained 0.15 parts by weight of leuco Malachite Green. After image-wise exposure, the resultant plate had a strong green image on a yellow background.

EXAMPLE 4

Example 3 was repeated except that Crystal Violet lactone was used in place of leuco Malachite Green. After image-wise exposure, the resultant plate had a strong violet image on a yellow background.

EXAMPLE 5

Example 2 (using the compound of Formula V) was repeated except that the plate was exposed for 60 seconds to light from a xenon arc through a Wratten 47B filter which transmits radiation in the range 380–490 nm. The developed image had a step-wedge reading of solid 6 tail 11.

EXAMPLE 6

A solution, in acetone, of a radiation sensitive composition comprising:
  3 parts by weight of DYNOMIN MM-80 (Dyno Industries), a melamine/formaldehyde resin, and
  0.15 parts by weight of the compound of Formula IV, was whirler coated on to a sheet of electrolytically grained and anodised aluminum and dried. The coating weight was 1 gm. per sq.m.

The resultant radiation sensitive plate was exposed through a continuous tone Stouffer step-wedge to ultraviolet light (20 units) from a Berkey Ascor printing down frame and baked for one minute at 80 degC. before being developed as described in Example 1. The resultant image had a step-wedge reading of solid 4 tail 9.

EXAMPLE 7

Example 6 was repeated except that the DYNOMIN MM-80 was replaced by ARALDITE Gy 250 (Ciba-Geigy), a Bisphenol A epoxy resin, and the compound of Formula I was used. The resultant image had a step-wedge reading of solid 3 tail 7.

EXAMPLE 8

A solution, in ethyl methyl ketone, of a radiation sensitive composition comprising:
- 4.5 parts by weight of novolak resin
- 10.4 parts by weight of N-vinyl carbazole
- 0.36 parts by weight of Sudan Yellow
- 0.15 parts by weight of the compound of Formula I was whirler coated on to a sheet of electrolytically grained and anodised aluminum and dried. The coating weight was 1 gm per sq.m.

The resultant radiation sensitive plate was exposed through a step-wedge on a Berkey Ascor frame (20 units) giving a red-image against a yellow background. The plate was developed using aqueous alkaline developer and gave a step-wedge reading of solid 3, tail 8.

EXAMPLE 9

A positive working radiation sensitive composition comprising:
- 6 g Naphthoquinone diazide sulphonic acid ester
- 27 g Novolak resin
- 0.48 g Compound of Formula I
- 0.36 g Sudan Yellow made up to 400 ml with 95/5 Acetone/Methyl Oxitol was whirler coated onto an electrolytically grained, sulphuric acid anodised, aluminum substrate to give a coating weight of 2.5 gm. per sq.m. The resultant radiation sensitive plate was then dried at 100 degC. for five minutes.

The plate was exposed through a Stouffer step-wedge on a Berkey-Ascor frame for 18 units (approx. 36 seconds), giving a yellow image against a red background. The plate was dish-developed in aqueous alkaline developer for 45 seconds. After inking, the image gave a step-wedge reading of clear 2 solid 7.

EXAMPLE 10

Example 9 was repeated using compounds of formulae VIII and VI. Each plate gave a step-wedge reading of clear 2, solid 7 after 18 units exposure on the Berkey Ascor frame. The contrast before development of the yellow image on the red background was the same for compound VIII as for compound I whereas the contrast for compound VI was not as good.

EXAMPLE 11

A positive working radiation sensitive composition was prepared from:
- 6 g Naphthoquinone diazide sulphonic acid ester
- 4 g Novolak resin
- 0.38 g Compound of Formula VIII
- 0.38 g Bromophenol Blue
- 0.19 g Triethylamine made up to 400 ml with 95/5 acetone/methyl oxitol.

The plate was prepared and developed as in Example 9.

An exposure of 10 units on the Berkey Ascor frame gave a plate with a pale grey image against a green background. After development and inking, the image gave a step-wedge reading of clear 2, solid 6.

EXAMPLE 12

A positive-working composition was prepared from
- 25.5 g Novolak resin
- 4.26 g Bis(2-tetrahydropyranyl)ether of Bisphenol A,
- 0.43 g Compound of Formula IX made up to 350 ml with ethyl methyl ketone.

The solution was whirler-coated as in Example 9 and dried at 65° C. for 10 minutes. The resulting radiation sensitive plate was exposed for 25 units in a Berkey Ascor frame and developed in aqueous alkaline developer for 75 seconds. After inking the image gave a step-wedge reading of clear 2, solid 9.

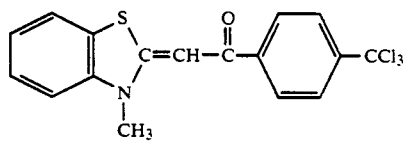

I

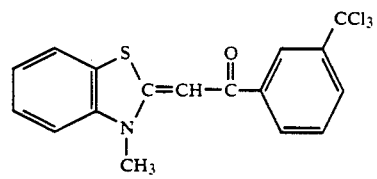

II

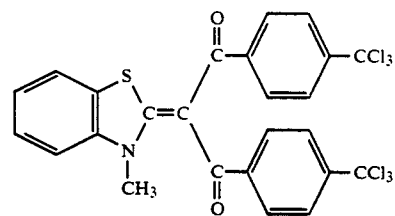

III

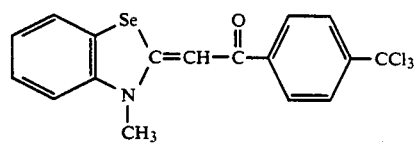

IV

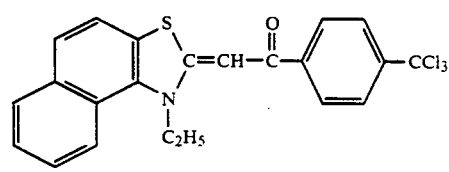

V

-continued
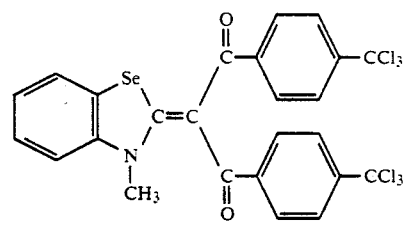 VI
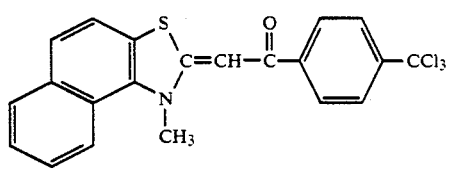 VII
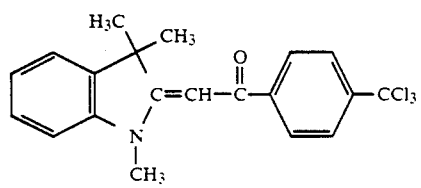 VIII
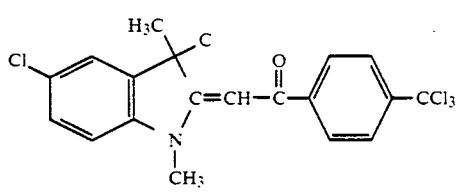 IX
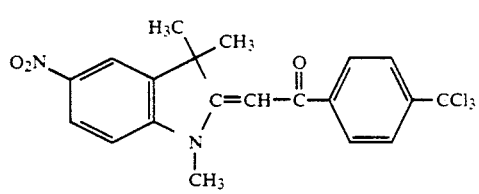 X
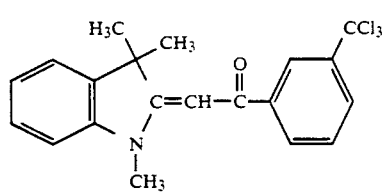 XI
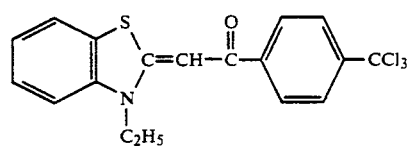 XII
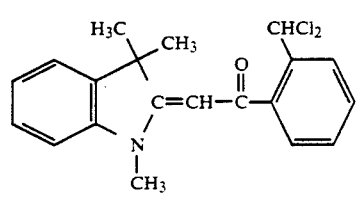 XIII
-continued
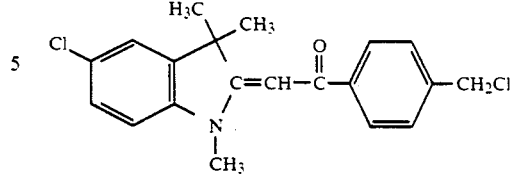 XIV
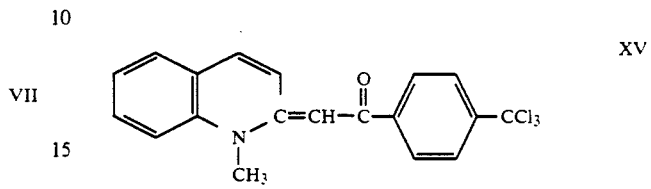 XV
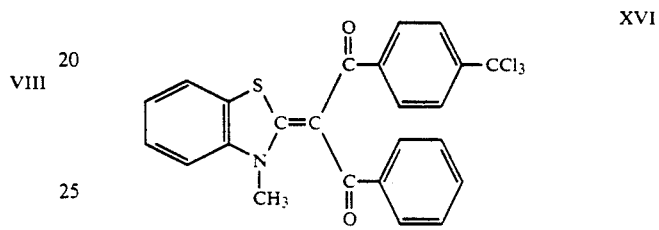 XVI
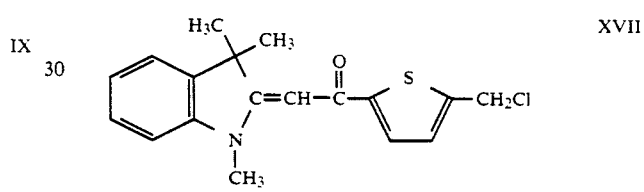 XVII
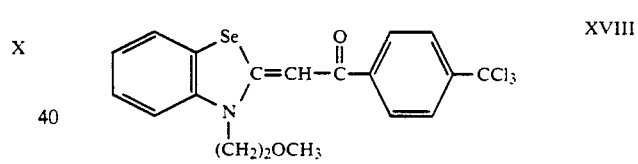 XVIII
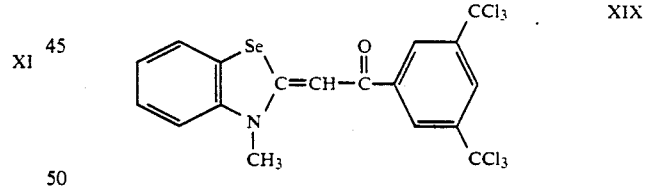 XIX
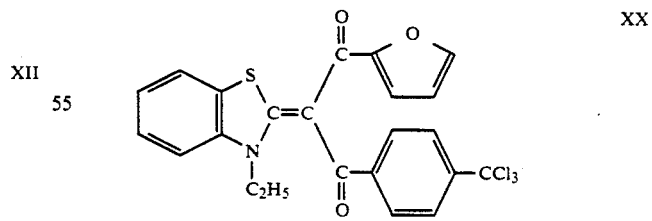 XX
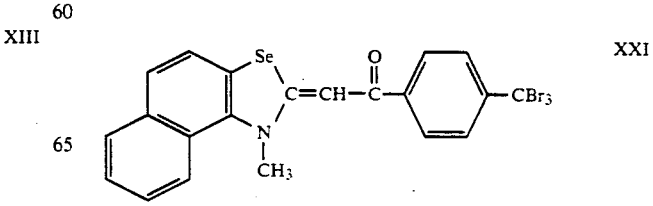 XXI

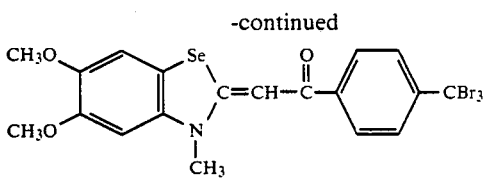

XXII

I claim:

1. A radiation sensitive composition comprising in admixture (i) a radiation sensitive compound having the general formula

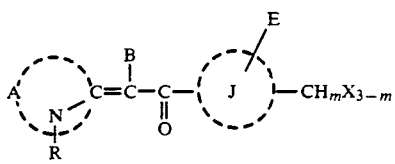

wherein
- A represents the ring members required to complete a 5- or 6-membered heterocyclic ring which may be fused to a substituted or unsubstituted aromatic nucleus,
- B represents H, acyl, aroyl, heterocyclyl, carbonyl or

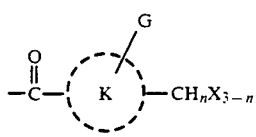

- R represents a substituted or unsubstituted alkyl group,
- E and G, which may be the same or different, each represents H, or $CH_pX_{3-p}$,
- J and K, which may be the same or different, each represents an aryl or heterocyclic group, which may include a substituent additional to E or G,
- X represents Cl or Br, and
- m,n and p, which may be the same or different, each represents an integer equal to 0, 1 or 2 and (ii) an additional ingredient selected from the group consisting of a photopolymerisable compound activated by free radicals, an acid hardenable material, a substance which undergoes a colour change when said compound is exposed to radiation, and an acid degradable compound, said radiation sensitive compound being present in the composition in an amount effective, on exposure of the composition to radiation, to cause said photopolymerisable compound to photopolymerise, said material to become hardened, said substance to undergo said colour change, and said acid degradable compound to become degraded, respectively.

2. A radiation sensitive composition as claimed in claim 1 wherein said radiation sensitive compound is in admixture with a photopolymerisable compound activated by free radicals.

3. A radiation sensitive composition as claimed in claim 1 wherein the photopolymerisable compound is an addition polymerisable compound containing ethylenic unsaturation.

4. A radiation sensitive composition as claimed in claim 1 wherein said radiation sensitive compound is in admixture with an acid hardenable material.

5. A radiation sensitive composition as claimed in claim 1 wherein said radiation sensitive compound is in admixture with a substance which undergoes a colour change when said compound is exposed to radiation.

6. A radiation sensitive composition as claimed in laid 1 wherein said substance is a dye, a dye precursor, or an indicator.

7. A radiation sensitive composition as claimed in claim 1 wherein said radiation sensitive compound is in admixture with an acid degradable compound.

8. A radiation sensitive plate comprising a substrate coated with a radiation sensitive composition comprising in admixture (i) a radiation sensitive compound having the general formula

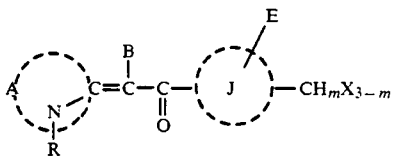

wherein
- A represents the ring members required to complete a 5- or 6-membered heterocyclic ring which may be fused to a substituted or unsubstituted aromatic nucleus,
- B represents H, acyl, aroyl, heterocyclyl, carbonyl or

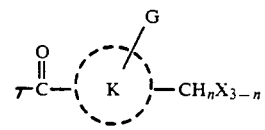

- R represents a substituted or unsubstituted alkyl group,
- E and G, which may be the same or different, each represents H or $CH_pX_{3-p}$,
- J and K, which may be the same or different, each represents an aryl or heterocyclic group, which may include a substituent additional to E or G,
- X represents Cl or Br, and
- m,n and p, which may be the same or different, each represents an integer equal to 0, 1 or 2 and (ii) an additional ingredient selected from the group consisting of a photopolymerisable compound activated by free radicals, an acid hardenable material, a substance which undergoes a colour change when said compound is exposed to radiation, and an acid degradable compound, said radiation sensitive compound being present in the composition in an amount effective, on exposure of the composition to radiation, to cause said photopolymerisable compound to photopolymerise, said material to become hardened, said substance to undergo said colour change, and said acid degradable compound to become degraded, respectively.

* * * * *